United States Patent
Hofmann

(10) Patent No.: US 11,911,235 B2
(45) Date of Patent: Feb. 27, 2024

(54) OCCLUSAL SPLINT ARRANGEMENT WITH A FIXING BAND

(71) Applicant: Konrad Hofmann, Thüngersheim (DE)

(72) Inventor: Konrad Hofmann, Thüngersheim (DE)

( * ) Notice: Subject to any disclaimer, the term of this patent is extended or adjusted under 35 U.S.C. 154(b) by 267 days.

(21) Appl. No.: 16/624,675

(22) PCT Filed: Jun. 21, 2018

(86) PCT No.: PCT/EP2018/066653
§ 371 (c)(1),
(2) Date: Dec. 19, 2019

(87) PCT Pub. No.: WO2018/234498
PCT Pub. Date: Dec. 27, 2018

(65) Prior Publication Data
US 2020/0129270 A1    Apr. 30, 2020

(30) Foreign Application Priority Data
Jun. 22, 2017   (DE) .................. 10 2017 113 833.1

(51) Int. Cl.
| A61C 7/08 | (2006.01) |
| A61C 7/36 | (2006.01) |
| A61F 5/56 | (2006.01) |

(52) U.S. Cl.
CPC ............ *A61C 7/08* (2013.01); *A61C 7/36* (2013.01); *A61F 5/566* (2013.01); *A61F 2005/563* (2013.01)

(58) Field of Classification Search
CPC .. A61C 7/08; A61C 7/36; A61C 5/007; A61F 5/566; A61F 2005/563
(Continued)

(56) References Cited

U.S. PATENT DOCUMENTS 4,619,609 A * 10/1986 Clark .................. A61C 7/00
                                                    433/6
5,755,219 A * 5/1998 Thornton ........ A61M 16/0493
                                                    128/201.18
(Continued)

FOREIGN PATENT DOCUMENTS

CH    707232 A1    5/2014
CN    203815696 U    9/2014
(Continued)

OTHER PUBLICATIONS

PCT International Search Report, PCT/EP2018/066653, dated Sep. 12, 2018, 7 pages.
(Continued)

*Primary Examiner* — Matthew M Nelson
(74) *Attorney, Agent, or Firm* — Quarles & Brady LLP

(57) ABSTRACT

An occlusal splint arrangement having a maxillary miniplast splint and a mandibular miniplast splint, and including a positioning means defining the position of the mandibular miniplast splint with respect to the maxillary miniplast splint in the x-direction. The positioning means is designed like a fixing band transmitting tensile forces, the two ends of the fixing band being fixed to two fastening elements, and the fastening elements being disposed in the left and the right molar region of the mandibular miniplast splint, and a middle section of the fixing band being guided at a guide means, and the guide means being disposed in the incisor region of the maxillary miniplast splint.

22 Claims, 17 Drawing Sheets

(58) Field of Classification Search
USPC .................................................... 433/6
See application file for complete search history.

(56) References Cited

U.S. PATENT DOCUMENTS

| | | | | |
|---|---|---|---|---|
| 5,947,724 | A * | 9/1999 | Frantz | A61F 5/566 |
| | | | | 128/848 |
| 6,027,340 | A * | 2/2000 | Chun | A61C 7/36 |
| | | | | 433/19 |
| 7,637,262 | B2 * | 12/2009 | Bailey | A61F 5/566 |
| | | | | 433/7 |
| 7,677,887 | B2 | 3/2010 | Nicholson | |
| 2010/0043805 | A1 * | 2/2010 | Kelly | A61F 5/566 |
| | | | | 433/213 |
| 2011/0277774 | A1 * | 11/2011 | Connell | A61F 5/566 |
| | | | | 128/848 |
| 2011/0308531 | A1 * | 12/2011 | Grosky | A61F 5/566 |
| | | | | 128/848 |
| 2014/0335468 | A1 * | 11/2014 | Dickerson | A61C 7/20 |
| | | | | 433/19 |
| 2015/0216716 | A1 * | 8/2015 | Anitua Aldecoa | A61C 7/36 |
| | | | | 29/428 |
| 2016/0038259 | A1 * | 2/2016 | Valceschini | A61F 5/566 |
| | | | | 433/6 |
| 2016/0067014 | A1 * | 3/2016 | Kottemann | A61C 7/36 |
| | | | | 433/24 |
| 2016/0199216 | A1 * | 7/2016 | Cam | A61F 5/566 |
| | | | | 128/848 |
| 2016/0331492 | A1 * | 11/2016 | Borovinskih | A61C 7/002 |
| 2017/0367793 | A1 * | 12/2017 | Veis | A61F 5/566 |
| 2020/0129270 | A1 * | 4/2020 | Hofmann | A61F 5/566 |

FOREIGN PATENT DOCUMENTS

| | | |
|---|---|---|
| DE | 10341260 A1 | 4/2005 |
| EP | 2143397 A1 | 1/2010 |
| JP | 2006095245 A | 4/2006 |
| KR | 20140011181 A | 1/2014 |
| KR | 101482728 B1 | 1/2015 |
| WO | 9725010 A1 | 7/1997 |
| WO | 2011120005 A2 | 9/2011 |
| WO | 2012038663 A1 | 3/2012 |
| WO | 2015118201 A1 | 8/2015 |

OTHER PUBLICATIONS

PCT English Language Translation of the International Preliminary Report on Patentability, PCT/EP2018/066653, dated Jan. 2, 2020, 9 pages.
Japan Patent Office, Notice of Reasons for Refusal, Application No. 2019-570111, dated Dec. 8, 2021, 11 pages.
Korean Intellectual Property Office, Notice of Rejection, Application No. 10-2019-7038687, dated Sep. 30, 2022, 12 pages.

* cited by examiner

OCCLUSAL SPLINT ARRANGEMENT WITH A FIXING BAND

CROSS-REFERENCE TO RELATED APPLICATIONS

This application represents the national stage entry of PCT International Patent Application No. PCT/EP2018/066653 filed on Jun. 21, 2018 and claims priority to German Patent Application No. DE 10 2017 113 833.1 filed Jun. 22, 2017. The contents of these applications are hereby incorporated by reference as if set forth in their entirety herein.

The disclosure relates to an occlusal splint arrangement, in particular for sleep apnea therapy, having a maxillary miniplast splint and a mandibular miniplast splint according to the preamble of claim 1.

Different embodiments of occlusal splint arrangements are known from the state of the art in particular for sleep apnea therapy. These occlusal splint arrangements basically aim to control the position of the maxilla with respect to the mandible to the effect that a returning of the mandible and the tongue muscle and the soft palate during deep sleep is limited to a tolerable degree by displacing the mandible forward (in the x-direction) in order to stretch the soft palate so much that the airways are kept open and sleep disorders due to insufficient supply with respiratory air are reduced and/or eliminated altogether.

A generic occlusal splint arrangement is known from DE 103 41 260 A1. This occlusal splint arrangement has a maxillary miniplast splint and a mandibular miniplast splint which can be placed on the corresponding row of teeth in the maxilla and the mandible, respectively. Furthermore, these miniplast splints have contact surfaces opposing each other which can be displaced labially in the x-direction and buccally in the y-direction in a transverse plane with respect to each other. The occlusal splint arrangement has an adjustment means having a locking pin and a locking guide in order to realize the definition of a determined position of the mandibular miniplast splint with respect to the maxillary miniplast splint. The position of the mandibular miniplast splint with respect to the maxillary miniplast splint is determined by the engagement of the locking pin with the locking guide. However, this occlusal splint arrangement has the disadvantage that, after the locking of the locking pin, a relative movement between the two miniplast splints is no longer possible at all, which significantly reduces the wearing comfort. Another disadvantage of this known occlusal splint arrangement is its complex design and the high production costs involved. Moreover, the occlusal splint arrangement is highly susceptible to dirt deposits in areas which are difficult to clean, making it difficult to ensure the necessary hygiene.

The object of the disclosure at hand is therefore to propose a new occlusal splint arrangement which allows a placement of the mandibular miniplast splint and the maxillary miniplast splint with respect to each other and avoids the disadvantages of the occlusal splint arrangements known from the state of the art.

This object is attained by an occlusal splint arrangement according to the teaching of claim 1.

Advantageous embodiments of the disclosure are the subject matter of the dependent claims.

The occlusal splint arrangement is preferably used for sleep apnea therapy. Although, thus, the embodiment at hand is primarily provided for therapy of the sleep apnea syndrome, in principle the occlusal splint arrangement according to the disclosure may also be used for other purposes.

The occlusal splint arrangement can, for example, also be intended for the treatment of malocclusions or as a bite splint to prevent teeth grinding at night. The occlusal splint arrangement according to the disclosure is characterized by the positioning means for the definition of the position of the mandibular miniplast splint with respect to the maxillary miniplast splint in the x-direction. The term 'definition of the position' is to be understood with a broad conceptual scope, to the effect that it is not a specific position that is defined, but a position of the two miniplast splints with respect to each other by means of which the desired effect can be attained. Actually, a certain residual mobility of the two rows of teeth in the maxilla and the mandible with respect to each other considerably increases the feeling of a subjective wearing comfort. In the occlusal splint arrangement according to the disclosure, a fixing band by means of which tensile forces can be transmitted serves as positioning means. The two ends of the fixing band are fixed to two fastening elements which are disposed in the molar region of the mandibular miniplast splint. At the same time, a middle section of the fixing band, which usually extends from the middle of the fixing band toward the ends, can be guided at a guide means which is disposed in the incisor region of the maxillary miniplast splint. By means of the guidance of the middle section of the fixing band in the incisor region of the maxillary miniplast splint, compressive forces can be transmitted from the middle section to the labially directed outside of the maxillary miniplast splint. At the same time, the two ends of the fixing band are fixed in the molar region of the mandibular miniplast splint such that also the ends of the fixing band can transmit tensile forces to the two fastening elements at the mandibular miniplast splint. As a result, depending on the length of the fixing band, it is thus possible to brace the mandibular miniplast splint forward with respect to the maxillary miniplast splint. The shorter the fixing band is chosen, the further the mandibular miniplast splint together with the mandible is pulled forward with respect to the maxillary miniplast splint and the maxilla.

One advantage of the occlusal splint arrangement according to the disclosure is that the result is a very simple design, which can be produced at little cost. Furthermore, the wearer of the occlusal splint arrangement retains a high degree of residual mobility between the two halves of the jaw after having placed the miniplast splint since only the returning of the mandible toward the palate is limited by the length of the fixing band. However, movements of the two miniplast splints with respect to each other in the lateral direction (y-direction) are not rigidly limited by the fixing band such that the wearer of the occlusal splint arrangement experiences a high wearing comfort.

It is generally optional in which way the fastening elements and the guide means are fixed to the mandibular miniplast splint and the maxillary miniplast splint, respectively. As very high demands are placed regarding the tolerance of different materials which are used for the production of the occlusal splint arrangement, it is particularly advantageous if the two fastening elements are integrally molded on or into the mandibular miniplast splint and/or the guide means is integrally molded on or into the maxillary miniplast splint. Due to the integral molding of the fastening elements and/or the guide means on or into each corresponding miniplast splint, the same material can be used for the production of the fastening elements and/or the guide means as for the production of the two miniplast splints themselves. The integral molding thereon or thereinto furthermore allows a high mechanical stability of the fastening elements and/or the guide means, which is very important with regard to an unintentional detachment of the fastening elements and/or the guide means.

The material of which the two fastening elements and the guide means are made is generally optional. It is particularly advantageous if the fastening elements are made of the same plastic material as the mandibular miniplast splints and the guide means is made of the same plastic material as the maxillary miniplast splint. Due to the use of the same plastic material for the two miniplast splints themselves as well as for the fastening elements and/or the guide means, tolerance problems can be precluded without any difficulty by additionally disposing the fastening elements and the guide means at the miniplast splints.

The production method by means of which the occlusal splint arrangements according to the disclosure are produced is generally optional. Thus, for the production of the occlusal splint arrangement, an impression of the teeth can be made and the two miniplast splints can be primary-formed on the model derived from said impression. Since the occlusal splint arrangement according to the disclosure having the two fastening elements at the mandibular miniplast splint and the guide means at the maxillary miniplast splint has a very simple design, it is, however, possible and basically very advantageous that the mandibular miniplast splint, together with the two fastening elements integrally molded thereon or thereinto, is produced in a 3D plastic printing process and/or that the maxillary miniplast splint, together with the guide means integrally molded thereon or thereinto, is produced in a 3D plastic printing process. Due to the production of the two miniplast splints in the 3D plastic printing process, impression errors, as they are nearly unavoidable in the production of an impression and the subsequent production of a model and the subsequent primary-forming of the miniplast splints on the models, can generally be precluded. Instead, the two rows of teeth are scanned with corresponding scanners and the geometry data collected in such a manner are used to control the 3D plastic printing process by means of known CAD/CAM methods. Furthermore, the production of the occlusal splint arrangement can be strongly rationalized by using 3D plastic printers.

As an alternative to the production in 3D plastic printing, the occlusal splint arrangement can also be produced by using a multi-axis milling process controlled by CAD.

The definition of the position of the mandibular miniplast splint with respect to the maxillary miniplast splint in the x-direction by the fixing band is primarily predetermined by the length of the fixing band. The shorter the fixing band, the further the mandibular miniplast splint, together with the mandible held thereon, is pulled forward and, thereby, the soft palate is stretched. In order to be able to adjust the position of the two miniplast splints with respect to each other in an easy manner, it is particularly advantageous if the fixing band is adjustable in length. By lengthening or shortening the fixing band, the position of the two miniplast splints with respect to each other can individually be adapted to the needs of each wearer. Alternatively, also several fixing bands having different lengths can be provided along with the occlusal splint arrangement in order to allow the user to correspondingly adjust the thereby attainable relative position of the two miniplast splints with respect to each other by choosing a certain fixing band.

The material of which the fixing band is made is generally optional. In order to preclude tolerance problems because of the material of the fixing band during wearing of the occlusal splint arrangement as easily as possible, it is particularly advantageous if the fixing band is made of a plastic material since plastic materials which are tolerable in the oral cavity can be obtained without any difficulty.

Regarding a reproducible and defined effect of the occlusal splint arrangement in sleep apnea therapy, it is very important that the soft palate continuously has a certain minimum stretch. In order to ensure this at any time, it is particularly advantageous that the fixing band is designed highly rigid in the direction of its longitudinal axis and substantially does not allow any elastic deformation under the occurring strains in the intended use. Thereby it is precluded that the mandible, also when the two rows of teeth unconsciously move against each other because of an undesired elasticity of the fixing band, is closed so much with respect to the maxilla that the stretch of the soft palate falls below the desired stretch.

According to a preferred embodiment, it is provided that the fixing band is made of an inherently stable, elastically deformable plastic material. The fixing band has an arcuate shape in the stress-free state. As a result, the preformed fixing band thus has a shape which approximately corresponds to the shape that the fixing band has after being fixed to the miniplast splints. Due to the deformation corresponding to the preset shape, the material stress in the material of the fixing band is considerably reduced such that the wearer does not have to deform the fixing band for the fixation to the miniplast splints at all or only minimally.

There is a plurality of options for the constructive design of the guide means and the fastening elements at the maxillary miniplast splint and the mandibular miniplast splint, respectively. According to a preferred embodiment, it is provided that the guide means of a mandibular miniplast splint is designed like a groove. Said groove then runs labially in the incisor region of the maxillary miniplast splint, i.e. at the outside of the miniplast splint and parallel to the dental arch. The fixing band can be inserted from the outside into said groove of the maxillary miniplast splint, such that the fixing band can transmit compressive forces to the groove base. By means of these compressive forces transmitted by the middle section of the fixing band to the groove base, the required tensile force in the fixing band can be built up, the mandibular miniplast splint being pulled forward with respect to the maxillary miniplast splint and being defined in its position by means of said tensile force.

If the fixing band, for example, is to be fixed in the groove of the miniplast splint by a press fit in a positive locking manner, it is advantageous if the fixing band is formed elastically deformable transversely to its longitudinal axis. Due to this elastic deformability of the fixing band, the fixing band can be compressed transversely to its longitudinal axis at least slightly and can be pressed through a constricted groove opening into the groove.

The length of the groove in the maxillary miniplast splint is to be so large that an adequate guidance of the fixing band at the maxillary miniplast splint is ensured at any time. At the same time, according to a preferred embodiment, between each one of the two ends of the groove in the maxillary miniplast splint and the respective one of the two fastening elements at the mandibular miniplast splint, a distance is to be present, in which the fixing band runs unguided with a free length section. By means of this free length section of the fixing band it is ensured that a displacement of the mandibular miniplast splint is made possible with respect to the maxillary miniplast splint at least in the y-direction, i.e. transversely to the stretching direction.

In order to be able to control the opening angle of the mandible with respect to the maxilla by means of the occlusal splint arrangement, it is advantageous if a distance is present between each one of the two lateral ends of the groove in the maxillary miniplast splint and the respective one of the two fastening elements at the mandibular miniplast splint, a right and a left deflection element being provided at the mandibular miniplast splint, at which the fixing band is deflected and by which the vertical relative movement between the maxillary miniplast splint and the mandibular miniplast splint is limited. As a result, it can be determined by means of the deflection elements how strongly the mandible is pulled against the maxilla.

According to a preferred embodiment, one or more constrictions are provided at the opening of the groove, by means of which the fixing band, which is in particular circular in the cross section, is fixed in a positive locking manner in the groove. As a result, the fit of the fixing band can thus be secured in the groove. This is in particular advantageous if the user first places the two miniplast splints, which are not connected to each other, on the maxilla and the mandible and, only after that, connects the two miniplast splints to each other by fixing the fixing band in the groove.

Furthermore, it is particularly advantageous if an insertion chamfer is provided at the outward facing side of the constrictions by means of which the fixing band is guided into the groove. This is in particular advantageous if the user first places the two miniplast splints, which are to not connected to each other, on the maxilla and the mandible and, only after that, connects the two miniplast splints to each other by fixing the fixing band in the groove.

It is very important for the function of the occlusal splint arrangement according to the disclosure, in particular in sleep apnea therapy, that the fixing band does not inadvertently become detached from the groove at the maxillary miniplast splint, for example during sleep, because, otherwise, the intended fixation of the mandibular miniplast splint with respect to the maxillary miniplast splint is no longer ensured. In order to ensure this securing of the fixing band in the groove, fixing pins and/or fixing webs can be provided at the opening of the groove, which constrict the opening of the groove in sections or along the full length of the groove. When the fixing band is inserted into the groove, the user then has the possibility to, for example, slightly elastically deform the fixing band and thereby press it through the constricted opening into the groove. It is precluded that the fixing band inadvertently becomes detached from the groove opening which is constricted by the fixing pins and/or fixing webs. If fixing pins are used in order to secure the fixing band and the groove, it is particularly advantageous if at least three fixing pins are provided. Fixing pins which are respectively adjacent to each other are alternately disposed at the side edges of the groove opposing each other with their free ends projecting into the opening in opposite directions, respectively. In order to insert the fixing band into the groove with the plurality of fixing pins designed in such a manner, the fixing band, which is initially not yet stretched, can be inserted into the groove, the fixing band being bent alternately upward and downward when passing the respectively adjacent fixing pins.

As an alternative to the use of fixing pins, fixing webs can also be provided at the opening of the groove for securing the fixing band. According to a preferred embodiment, these fixing webs can extend continuously between the two lateral ends of the groove. The opening cross section between the two fixing webs should then be at least so large that inserting the fixing band into the groove is made possible when the cross section of the fixing band is deformed in a tolerable manner.

According to a preferred embodiment, it is provided that the cross section of the groove is at least slightly smaller than the cross section of the fixing band, the fixing band being fixed in the groove by the press fit formed thereby. Due to the friction between the groove surface and the fixing band, the press fit ensures that the fixing band can no longer be displaced after it has been pressed into the groove base.

A press fit can be realized particularly effectively if the fixing band has a circular cross section.

When the mandibular miniplast splint moves with respect to the maxillary miniplast splint in the y-direction, i.e. transversely to the stretching direction, the two fastening elements at the mandibular miniplast splint are displaced with respect to the maxillary miniplast splint in the y-direction. In order to not restrict this movement in an undesirable manner, it is particularly advantageous if the cross section of the groove is larger than the cross section of the fixing band, such that no substantial frictional locking occurs between the fixing band and the groove surface. In this way, the fixing band can then be displaced in the groove along its longitudinal axis substantially without resistance such that the movement of the mandibular miniplast splint in the y-direction is not impeded by the frictional locking of the fixing band in the groove. The stretching effect of the fixing band according to the disclosure on the mandibular miniplast splint is not impaired thereby as it is only necessary to transmit the compressive forces from the fixing band to the groove base for achieving this stretching effect. In order to secure the fixing band in the groove, according to another variant it is also possible that the fixing band has a rectangular cross section, the width of the fixing band being larger than the opening cross section of the groove and the height of the fixing band being smaller than the opening cross section of the groove. When the fixing band is inserted into the groove, the fixing band is held in such a manner that it is inserted with its narrower side widthways into the opening cross section of the groove. As soon as the fixing band extends across the full length of the groove, it can be rotated through 90° such that a pulling back of the fixing band through the opening cross section because of the large width of the fixing band is precluded. The fit of the fixing band in this position can then be secured by hooking the ends of the fixing band onto the fastening means of the mandibular miniplast splint.

Preferably, the fixing band in the incisor region should run parallel to the outside of the incisors, i.e. parallel to the dental arch, with the longitudinal side of the rectangular cross section since, thus, it is ensured that the fixing band has the maximum rigidity in the direction of the largest transverse strain.

The manner in which the two fastening elements are formed at the mandibular miniplast splint is generally optional. To realize the fastening elements, it is particularly easy and cost-effective if said fastening elements are designed like fixing pins which project laterally in the molar region of the mandibular miniplast splint. The free length of these fixing pins can be very short since only a relatively small projection of the fixing pins is required for fixing the ends of the fixing band. Furthermore, such fixing pins can be integrally molded on the plastic material of the mandibular miniplast splint very easily, in particular in the 3D plastic printing process. The geometry of the fixing pins is to be chosen such that the ends of the fixing band can be hooked onto the fixing pins with a recess or a hook element in a fixing manner.

In order to preclude an unintentional detachment of the ends of the fixing band from the fixing pins, according to a preferred embodiment a securing element is provided at the free end of the fixing pins. Said securing element can, for example, be designed like an enlargement whose cross section is larger than the cross section of a recess at the end of the fixing band, with which the fixing band is hooked onto the fixing pin. The material of the fixing band then has to have such a large deformability that the end of the fixing band having the recess provided therein can be pushed onto the fixing pin by overcoming the enlargement.

It is preferred that at least one projection is provided at each free end of the fixing pins, the projection, in a mounting position of the fixing band, being inserted into an opening at the end of the fixing band, and the projection, in a fixing position of the fixing band, engaging in a fixing manner behind the opening at the end of the fixing band. As a result, by correspondingly turning the ends of the fixing band, the user can thus hook said fixing band in a not yet connected state onto the fixing pin without any difficulty. In the usage position of the fixing band, the ends of the fixing band are then in the fixing position such that an unintentional detachment of the ends of the fixing band from the fixing pins is reliably precluded because of the projections engaging therebehind.

In particular in the case of preformed fixing bands, it has to be ensured that the fixing band is hooked onto the fixing pins in correct positional arrangement corresponding to its deformation. In order to ensure this, the securing element at the right fixing pin can have a different shape than the securing element at the left fixing pin. In particular, the enlargement at the right fixing pin can have a different diameter than the enlargement at the left fixing pin. The opening at the left end of the fixing band is adapted to the shape of the securing element at the left fixing pin and the opening at the right end of the fixing band is adapted to the shape of the securing element at the right fixing pin such that the user can thus hook the ends of the fixing band onto the fixing pins only in correct positional arrangement.

With sensitive users, the fastening elements laterally projecting at the mandibular miniplast splints can cause irritations of the oral mucosa in the molar region. In order to prevent these irritations of the oral mucosa, according to a preferred variant smooth cover elements are provided adjacent to each fastening element at the mandibular miniplast splint, said cover elements projecting beyond the miniplast splint in correspondence with the fastening elements and, in this way, laterally cover the fastening elements at least partially. Due to their smoothness, the cover elements can substantially reduce and/or entirely preclude the irritation of the oral mucosa.

In order to be able to adapt the occlusal splint arrangement to the individual needs of a patient, it is advantageous if markings that indicate the position of the two miniplast splints with respect to each other are attached to the two miniplast splints. In this way, in particular the choice of a fixing band having a suitable length is made easier.

Different embodiments of the disclosure are schematically illustrated in the drawings and are explained in an exemplary manner below.

Figure 1:
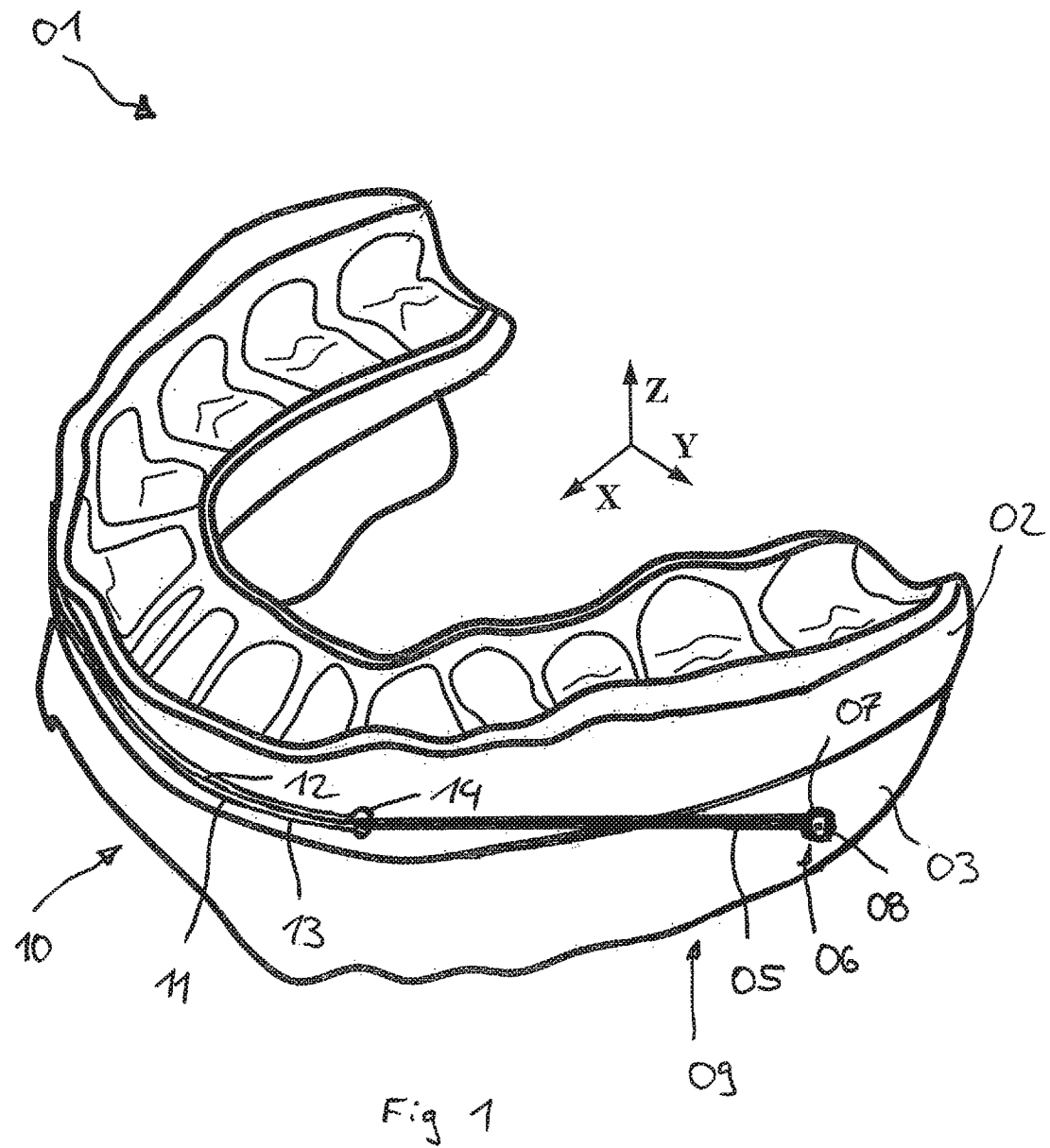
FIG. 1 shows a perspective view from above of an occlusal splint arrangement having a fixing band for defining the position between the mandibular miniplast splint and the maxillary miniplast splint.

FIG. 1 shows an occlusal splint arrangement 01 as it can be used for sleep apnea therapy, for example. The occlusal splint arrangement 01 comprises a maxillary miniplast splint 02 for being disposed on the row of teeth of the maxilla and a mandibular miniplast splint 03 for being disposed on the row of teeth of the mandible. The two miniplast splints 02 and 03 can be displaced labially in the x-direction and buccally in the y-direction in the transverse plane 04 (see FIG. 2) with respect to each other.

In order to be able to achieve, in the context of sleep apnea therapy, an increase of the stretching in the soft palate, it is required that the mandibular miniplast splint 03 is pulled forward in the x-direction with respect to the maxillary miniplast splint 02 and is held there. A fixing band 05 serves to define the position to be maintained between the mandibular miniplast splint 03 and the maxillary miniplast splint 02. Each one of the two ends 06 of the fixing band 05 has an annular recess 07 and can be hooked onto a respective one of fastening elements 08, which are integrally molded on the mandibular miniplast splint 03. In FIG. 1 only the one end 06 of the fixing band 05 is illustrated. In the same manner the second end 06 of the fixing band 05 is hooked onto a second fastening element 08 having a recess 07 on the right side of the mandibular miniplast splint 03. The two fastening elements 08 are disposed in the molar region 09 of the miniplast splint 03 and project buccally from the side surface of the miniplast splint 03.

The maxillary miniplast splint 02 has a guide means 11 in the incisor region 10, in which 11 a middle section 12 of the fixing band 05 is guided. The guide means 11 is designed like a groove 13 (see FIG. 8) and extends between its ends 14, of which only the left end 14 is illustrated in FIG. 1, through the plastic material of the maxillary miniplast splint 02.

When the two ends 06 of the fixing band 05 are hooked onto the fastening elements 08 of the mandibular miniplast splint 03 and when the middle section 12 of the fixing band 05 runs through the groove 13, then, depending on the length of the fixing band 05, the mandibular miniplast splint 03 can be stretched forward in the x-direction with respect to the maxillary miniplast splint 02 in order to thereby control the desired stretch of the soft palate.

Figure 2:
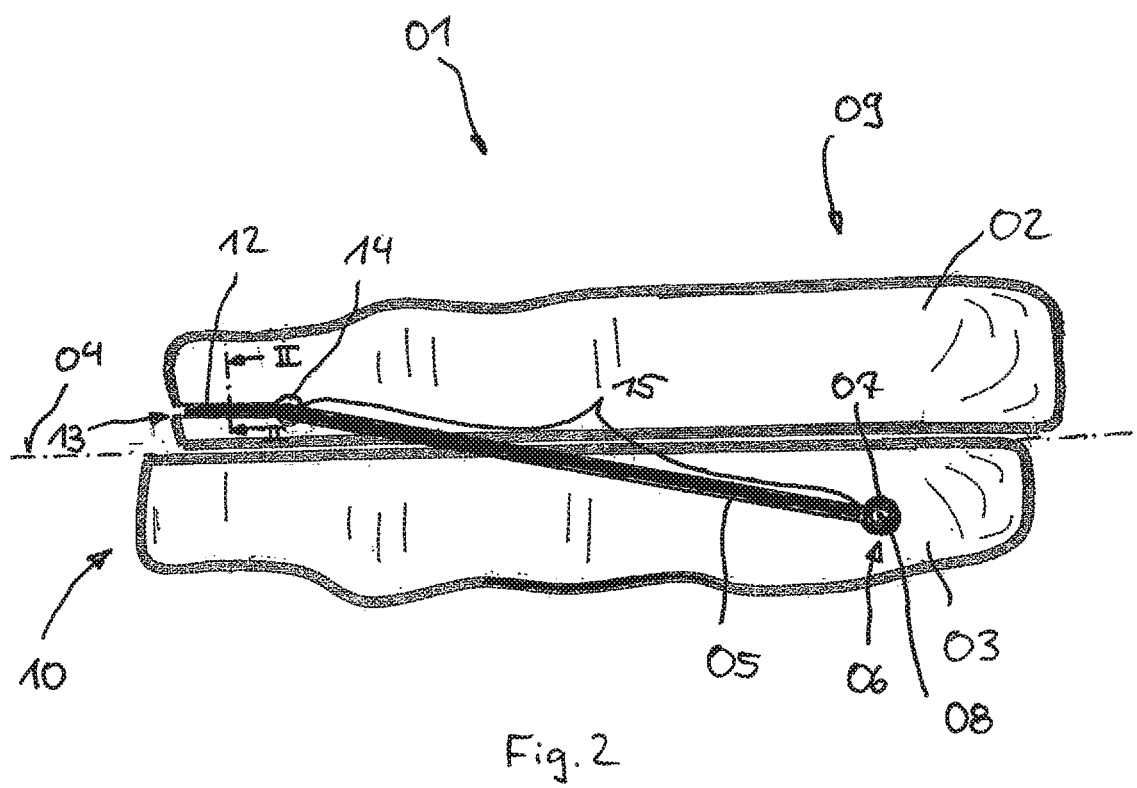
FIG. 2 shows a side view of an occlusal splint arrangement according to FIG. 1.

FIG. 2 shows a side view of the occlusal splint arrangement 01 having the two miniplast splints 02 and 03. The fixing band 05 is made of a plastic material which is deformable transversely to its longitudinal axis, but highly rigid in the longitudinal direction such that the fixing band 05 substantially cannot be stretched elastically in the tensile direction. In this way, it is precluded that the user pulls the miniplast splint 03 backward against the stretching direction while elastically deforming the fixing band 05 by applying corresponding muscle forces. At the same time, a free length section 15 is present between the end 14 of the groove 13 on the one hand and the fastening element on the other hand, in which 15 the fixing band runs unguided on the left side and on the right side of the occlusal splint arrangement 01 between the two miniplast splints 02 and 03. This free length section 15 of the fixing band 05 allows a movement of the two miniplast splints 02 and 03 in the transverse plane transversely to the x-direction, that is to say in the y-direction.

Figure 3:
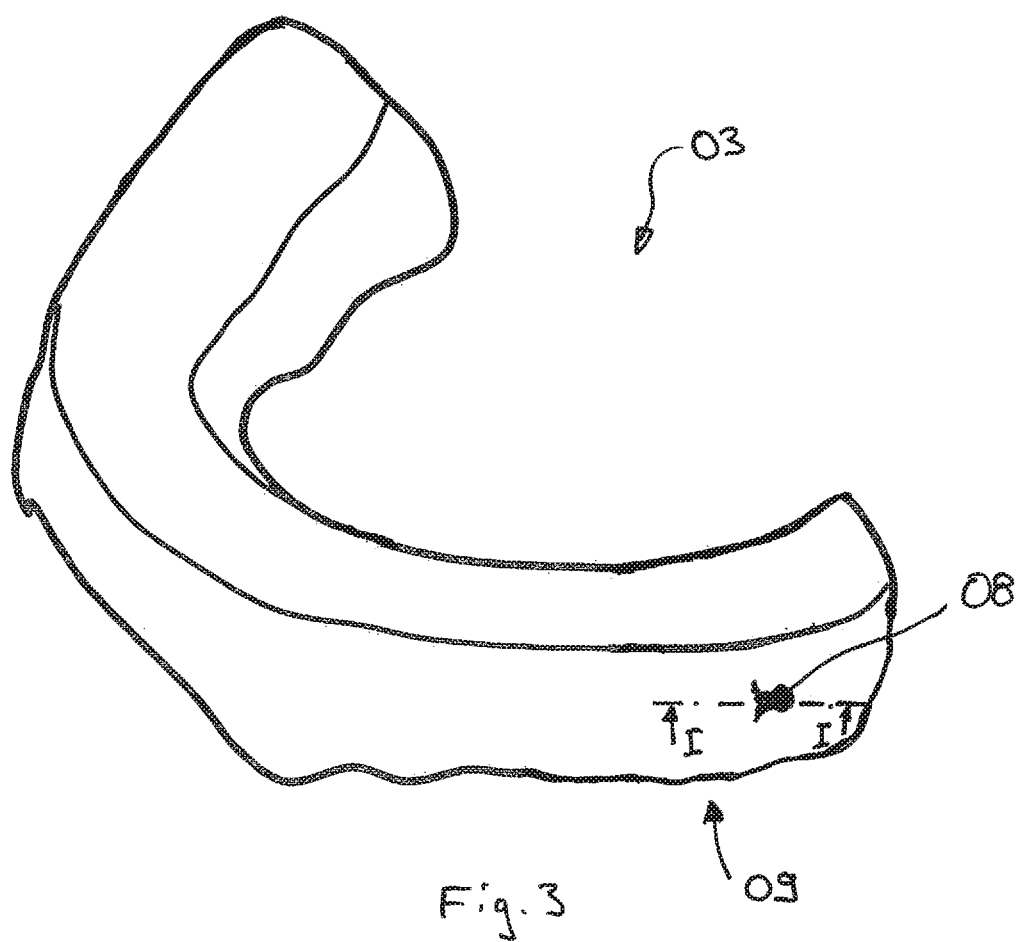
FIG. 3 shows a perspective view from above of the mandibular miniplast splint of the occlusal splint arrangement according to FIG. 1.

FIG. 3 shows a perspective view of the mandibular miniplast splint 03 having the fastening element 08 disposed in the molar region 09. The fastening element 08 is made of the same plastic material as the mandibular miniplast splint 03 itself. The design of the fastening element 08 is explained in more detail below with reference to the drawings FIG. 4 and FIG. 5.

Figure 4:
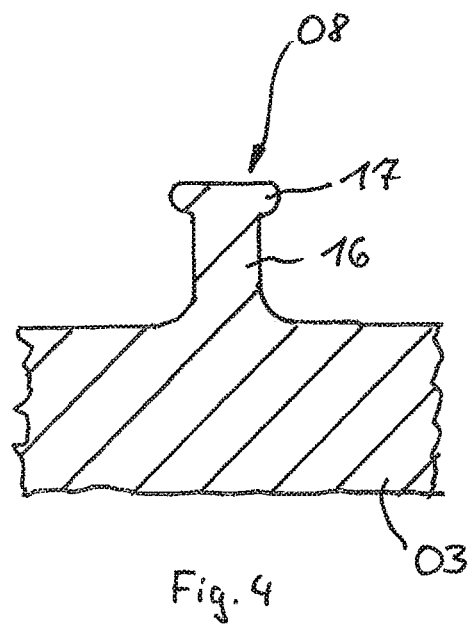
FIG. 4 shows a partial cross section along the intersection line I-I of the fastening element of the mandibular miniplast splint according to FIG. 3.

FIG. 4 shows a partial cross section along the intersection line I-I of the fastening element 08 of the mandibular miniplast splint 03. The fastening element 08 is designed like a fixing pin 16 which projects laterally from the miniplast splint 03. The fixing pin 16, and thus the fixing element 08, is integrally molded on the miniplast splint 03 and is made of the same plastic material as the miniplast splint 03. The miniplast splint 03 having the fastening element 08, that is to say the fixing pin 16, can be produced particularly easily and cost-effectively by means of 3D plastic printing. A securing element 17 which is designed like an enlargement of the fixing pin 16 is located at the free end of the fixing pin 16.

Figure 5:
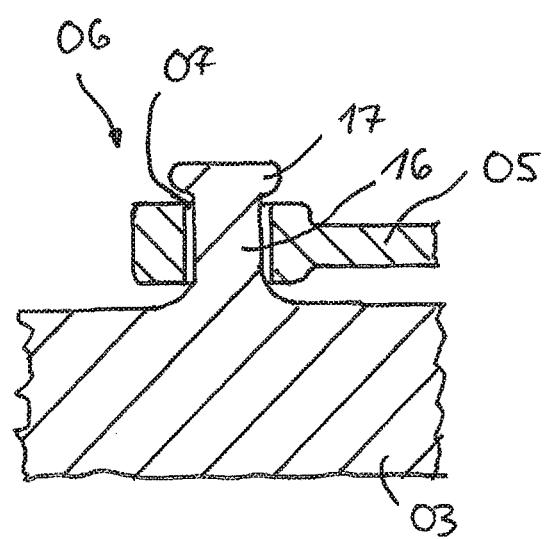
FIG. 5 shows the fastening element according to FIG. 4 after the end of a fixing band has been attached.

FIG. 5 shows the fixing pin 16 after the fixation of the fixing band 05 by pushing the recess 07 onto the fixing pin 16. An unintentional detachment of the fixing band 05 from the fixing pin 16 is impeded by the securing element 17, which has a larger cross section than the recess 07.

Figure 6:
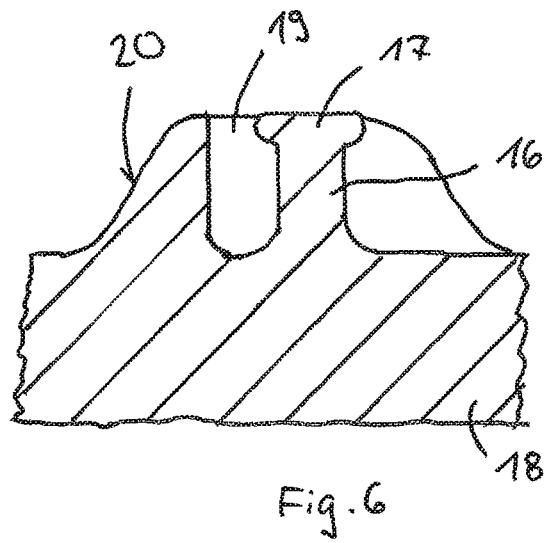
FIG. 6 shows a partial cross section of a second embodiment of a fastening element for arrangement at a miniplast splint.

FIG. 6 shows an alternative embodiment 18 of a miniplast splint on which a fixing pin 16 is also integrally molded. In contrast to the miniplast splint 03, a cover element 19 is integrally molded on the miniplast splint 18, which 19 is disposed adjacent to the fixing pin 16. The cover element 19 projects beyond the miniplast splint 18 with the same free length as the fixing pin 16 and covers the fixing pin 16 with a smooth side surface 20. Irritations of the mucosa in the molar region during wearing of the mandibular miniplast splint 18 can be avoided because of the covering of the same with the cover element 19.

Figure 7:
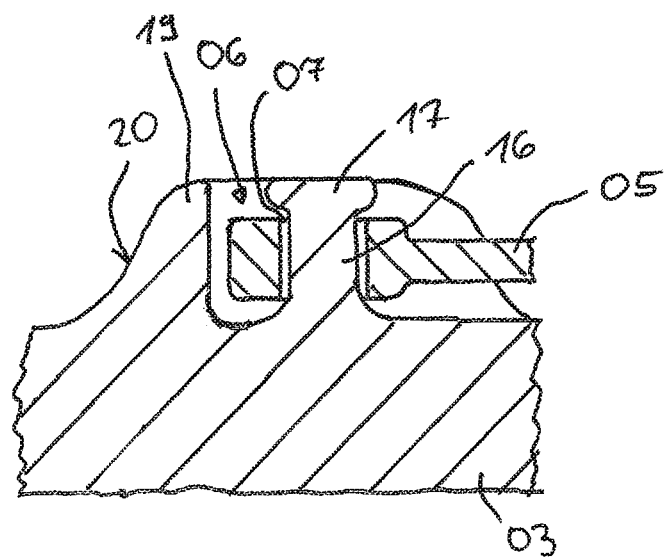
FIG. 7 shows the fastening element according to FIG. 6 after the end of a fixing band has been attached.

FIG. 7 shows the mandibular miniplast splint 18 having the fixing pin 16 and the cover element 19 after the fixing band 05 has been attached to the fixing pin 16.

Figure 8:
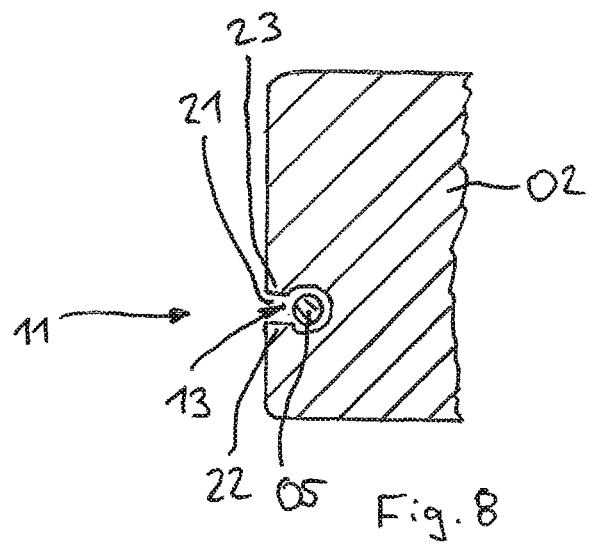
FIG. 8 shows a partial cross section along the intersection line II-II of the maxillary miniplast splint of the occlusal splint arrangement according to FIG. 2.

FIG. 8 shows a partial cross section along the intersection line II-II (see FIG. 2) of the maxillary miniplast splint 02. The guide means 11 at the miniplast splint 02 is formed by the groove 13 which is integrally molded into the plastic material of the maxillary miniplast splint 02. This can be produced very easily and cost-effectively by means of 3D plastic printing. The cross section of the groove 13 is slightly larger than the cross section of the fixing band 05 such that the fixing band can be displaced in the groove along its longitudinal axis substantially without resistance because substantially no frictional locking is present between the fixing band 05 and the inside of the groove 13. Two fixing webs 22 and 23 which constrict the opening 21 of the groove 13 are provided at the opening 21 of the groove 13. The remaining opening cross section of the opening 21 is slightly smaller than the cross section of the fixing band 05 such that a slipping out of the fixing band 05 from the groove 13 during wearing of the occlusal splint arrangement 01 is precluded.

Figure 9:
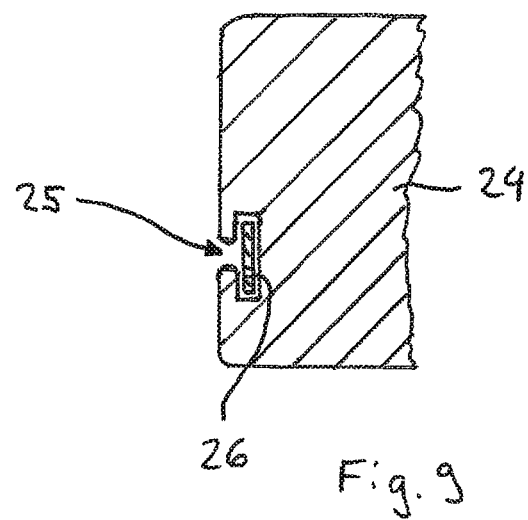
FIG. 9 shows a partial cross section of a second embodiment of a miniplast splint.

FIG. 9 shows an alternative embodiment 24 of a maxillary miniplast splint whose guide means is again designed like a groove 25. A rectangular fixing band 26 is guided in the groove 25, the width of the fixing band 26 being larger than the opening cross section of the groove 25 and the height of the fixing band 26 being smaller than the opening cross section of the groove 25. In order to insert the fixing band 26, said fixing band 26 is rotated through 90° in contrast to the illustration in FIG. 8 and is threaded in the groove 25 with one side edge. The fixing band 26 in the groove 25 is then again rotated back through 90° and, due to the larger width with respect to the opening cross section of the groove 25, can no longer slip out of the groove 25 during wearing of the maxillary miniplast splint 24. The fixing band has a high rigidity in the direction of the main strain because it runs in the incisor region with the longitudinal side of its rectangular cross section parallel to the outside of the incisors, i.e. parallel to the dental arch.

Figure 10:
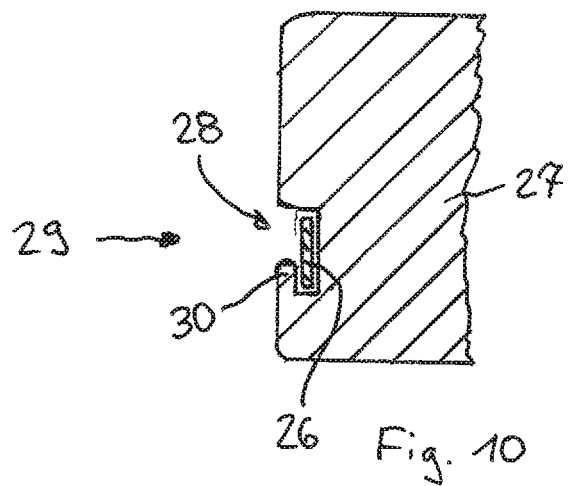
FIG. 10 shows a partial cross section of a third embodiment of a miniplast splint.
Figure 11:
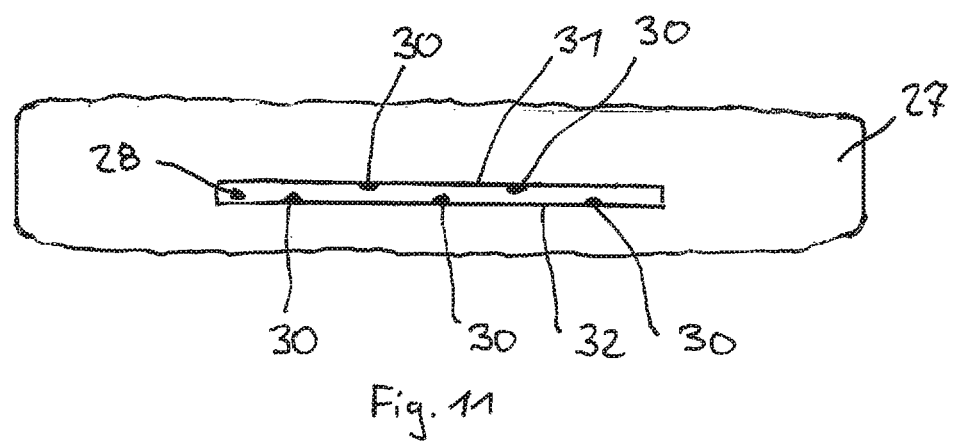
FIG. 11 shows a front view of the miniplast splint according to FIG. 10.

FIG. 10 and FIG. 11 show another embodiment 27 of a maxillary miniplast splint which again comprises a groove 28 as guide means 29. In order to secure the fixing band 26 in the groove 28, the miniplast splint 27 comprises integrally molded fixing pins 30 each of which projects from a side into the opening of the groove 28 and changes the opening cross section.

As can be seen from FIG. 11, the different fixing pins 30 are respectively disposed alternately at the upper side edge 31 and the lower side edge 32 of the groove 28 such that the fixing band 26 can be inserted into the groove 28 correspondingly more easily.

Figure 12:
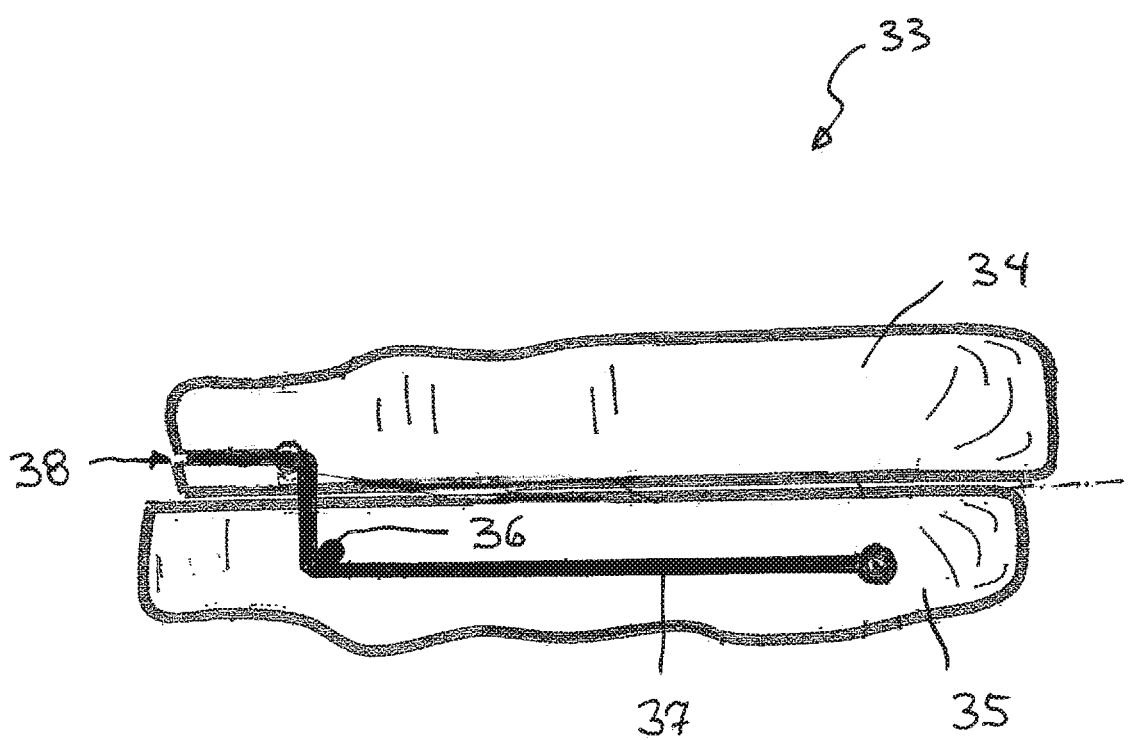
FIG. 12 shows a side view of a second embodiment of an occlusal splint arrangement.

FIG. 12 shows a side view of a second embodiment 33 of an occlusal splint arrangement. The basic design of the occlusal splint arrangement 33 having two miniplast splints 34 and 35 corresponds to the design of the occlusal splint arrangement 01 as it is illustrated in FIG. 2. However, in contrast to the case of the occlusal splint arrangement 01, in the occlusal splint arrangement 33 a deflection element 36 is provided at the mandibular miniplast splint 35, at which 36 a fixing band 37 can be deflected after the groove 38 has been hooked onto the maxillary miniplast splint 34. In FIG. 12 only the left deflection element 36 is illustrated. A corresponding right deflection element is located at the opposing side of the mandibular miniplast splint 35. By means of the two deflection elements 36 provided at the mandibular miniplast splint 35, the mandibular miniplast splint 35, and thus the mandible, can be pulled toward the maxillary miniplast splint 34, and thus toward the maxilla, and thereby the opening angle of the mandible can be limited with respect to the maxilla.

Figure 13:
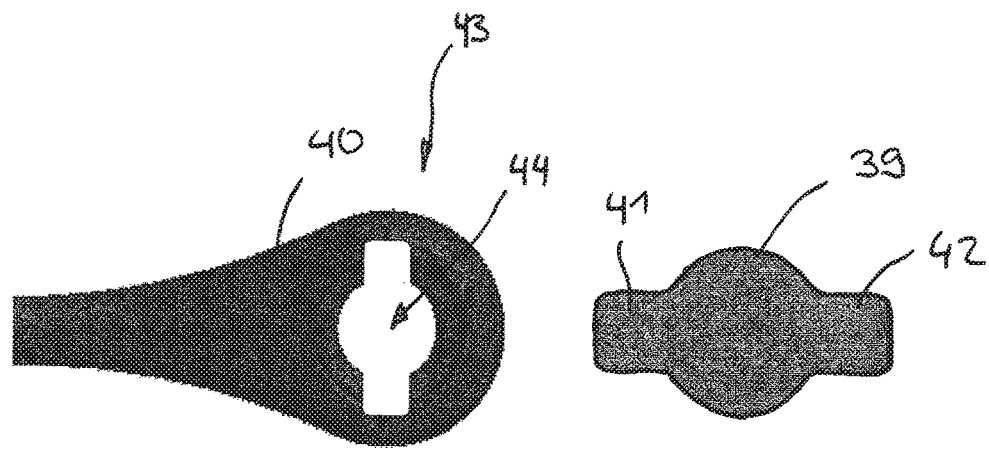
FIG. 13 shows a top view of a second embodiment of a fastening element of a mandibular miniplast splint with an end of the associated fixing band.

FIG. 13 shows a second embodiment 39 of a fastening element at a mandibular miniplast splint. Next to the fastening element 39, the end of the associated fixing band 40 is illustrated. The fastening element 39 is designed like a fixing pin and is shown in FIG. 13 in a top view. Two projections 41 and 42 are molded on the fastening element 39, which 41, 42 project laterally beyond the main body of the fixing pin. At the end 43 of the fixing band 40 an opening 44 is provided whose contour corresponds to the contour of the fastening element 39 in the area of the projections 41 and 42. By turning the end 43 through 90°, the fixing pin of the fastening element 39 can be inserted into the opening 44 and can then be fixed by rotating the end 43 back through 90°. In their fixing position the projections 41 and 42 engage behind the edge of the opening 44 and thereby prevent an unintentional detachment of the fixing band 40 from the fastening element 39.

Figure 14:
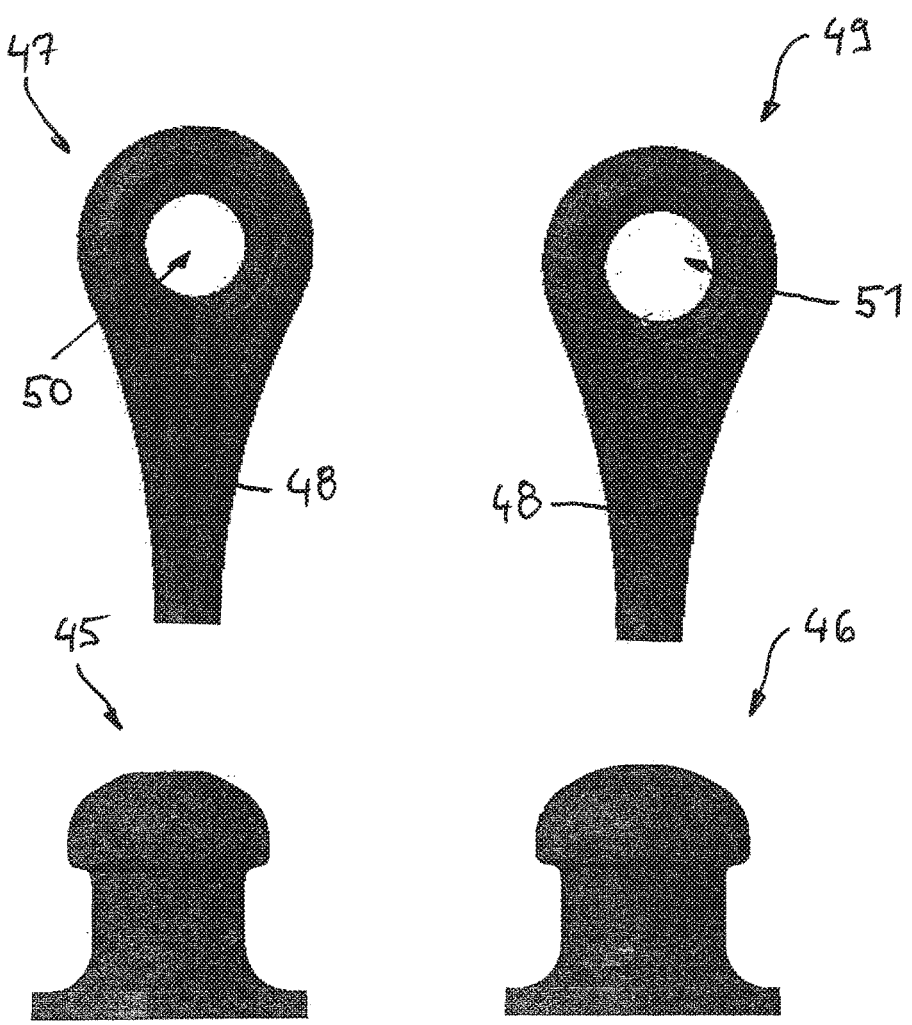
FIG. 14 shows a top view of a third embodiment of the right and the left fastening element of a mandibular miniplast splint with the right and left ends of the associated fixing band.

FIG. 14 shows a third embodiment of fastening elements 45 and 46 each of which is designed like a fastening pin. The left end 47 of a fixing band 48 is assigned to the left fastening element 45. The right end 49 of the fixing band 48 is assigned to the right fastening element 46. The opening 50 at the left end 47 of the fixing band 48 is smaller in the cross section than the opening 51 at the right end 49 of the fixing band 48. Correspondingly, the fixing pin at the left fastening element 45 and the fixing pin at the right fastening element 46 also have different diameters such that the opening 50 can be pushed onto the fastening element 45 and the opening 51 can be pushed onto the fastening element 46 and thus the fixing band 48 can be hooked thereonto on the left and on the right. Due to the different diameters of the openings 50 and 51 it is, however, precluded that the left end 47 is inadvertently hooked onto the right fastening element 46 because the difference in diameter is too large for the left end 47 with its opening 50 to be hooked onto the right fastening element 46. Thus, it is precluded that the fixing band 48 is hooked onto the fastening elements 45 and 46 in wrong positional arrangement.

Figure 15:
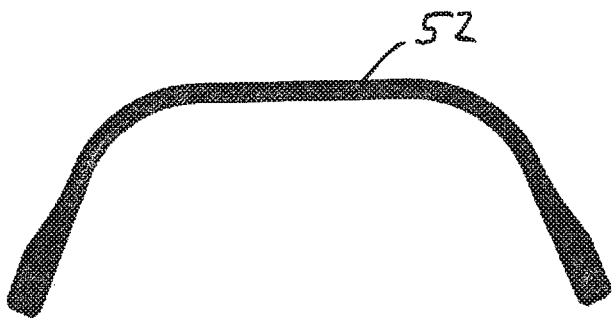
FIG. 15 shows a top view of a preformed fixing band.
Figure 16:
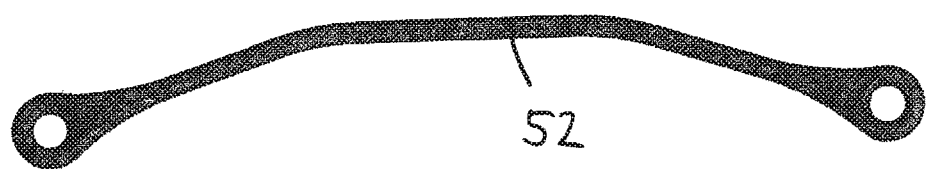
FIG. 16 shows a side view of the preformed fixing band according to FIG. 15.

FIG. 15 and FIG. 16 show a top view and a front view, respectively, of an embodiment 52 of a preformed fixing band. Due to the arcuate preformation of the fixing band 52, the shape of said fixing band 52 in the stress-free state exactly corresponds to the arcuate shape that the fixing band 52 assumes when being fixed to an occlusal splint arrangement 01. In this way, stretching strains caused by a deformation of the fixing band 52 as they occur in not preformed fixing bands are avoided.

Figure 17:
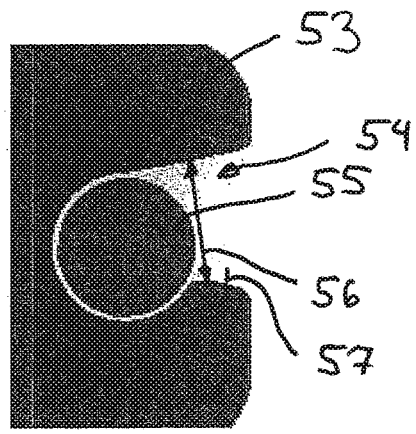
FIG. 17 shows a cross section of a fixing band fixed in a groove by a press fit.
Figure 18:
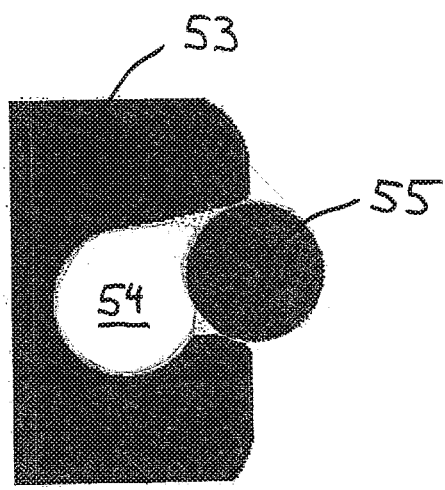
FIG. 18 shows a cross section of the fixing band according to FIG. 17 when being inserted into the groove according to FIG. 17.

FIG. 17 and FIG. 18 show a partial cross section of a maxillary miniplast splint 53 in the area of the groove 54 in order to accommodate a fixing band 55 which is circular in the cross section in a fixing manner. The fixing band 55 is made of a plastic material which is elastically deformable transversely to its longitudinal axis. The opening 56 of the groove 54 is designed like a constriction such that the opening cross section of the opening 56 is smaller than the outside diameter of the fixing band 55. If the fixing band 55 is pressed from the outside toward the groove 54, as it is illustrated schematically in FIG. 18, a deformation resistance, by means of which the fixing band 55 is slightly flattened such that said fixing band 55 slides into the groove 54, has to be overcome. In order to make it easier to insert the fixing band 55 into the groove 54, an insertion chamfer 57 is provided at the outward facing side of the opening 56 designed as a constriction. As soon as the fixing band 55 is completely accommodated in the groove 54, a positive locking press fit is formed such that the fixing band 55 can be moved with respect to the groove 54 only by overcoming a corresponding frictional resistance.

Figure 19:
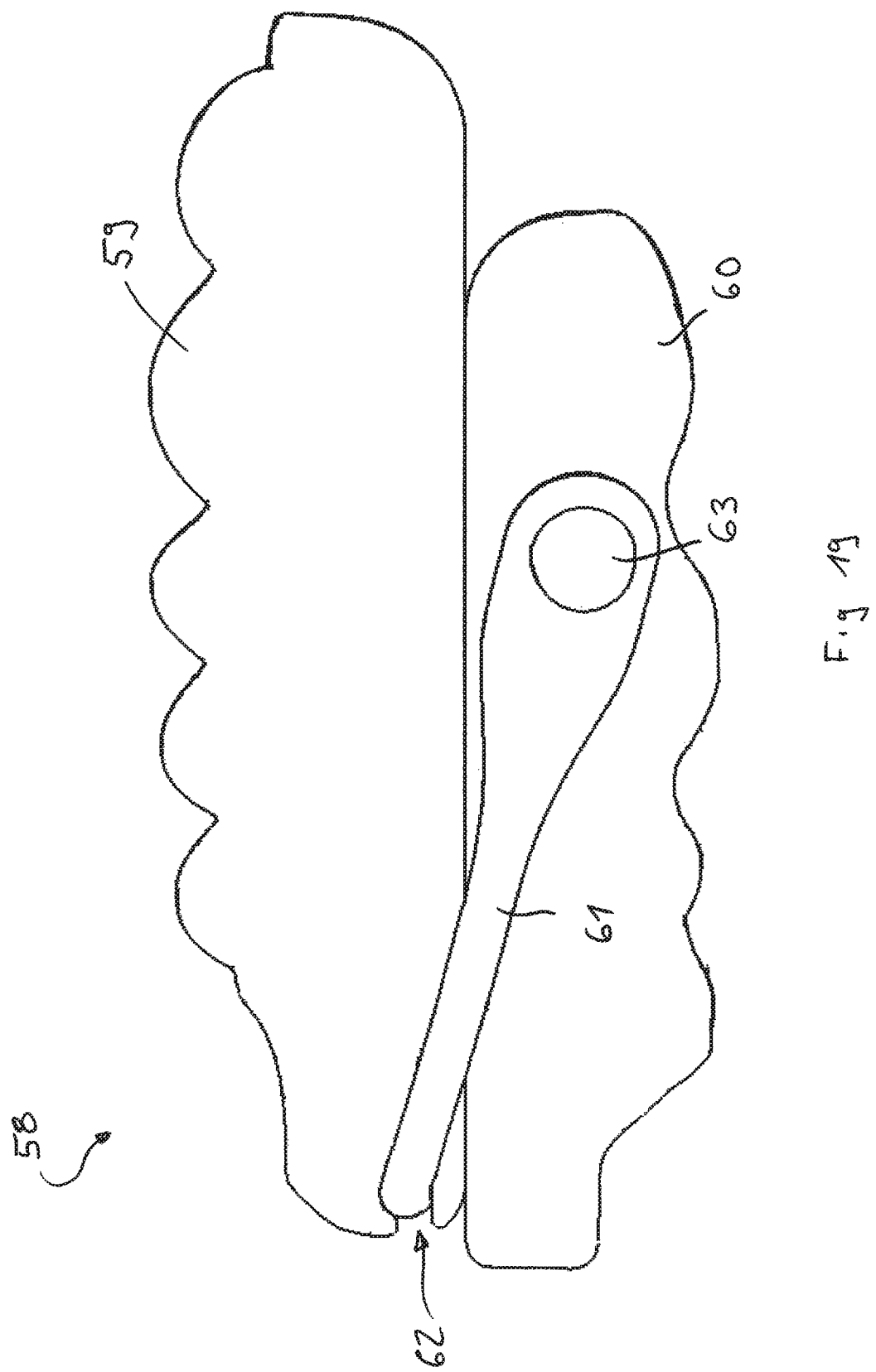
FIG. 19 shows a side view of a third embodiment of an occlusal splint arrangement.

FIG. 19 shows a side view of a third embodiment 58 of an occlusal splint arrangement. The basic design of the occlusal splint arrangement 58 having two miniplast splints 59 and 60 corresponds to the design of the occlusal splint arrangement 01 as it is illustrated in FIG. 2.

In the occlusal splint arrangement 58 a fixing band 61 is provided in order to connect the maxillary miniplast splint 59 and the mandibular miniplast splint 60, which 61 can be fixed in a groove 62 of the maxillary miniplast splint 59. The ends of the fixing band 61 are fixed at the fastening elements 63 and 64. The fastening elements 63 and 64 made of a plastic material are integrally molded onto the mandibular miniplast splint 60 and can be produced from plastic material in 3D printing.

Figure 20:
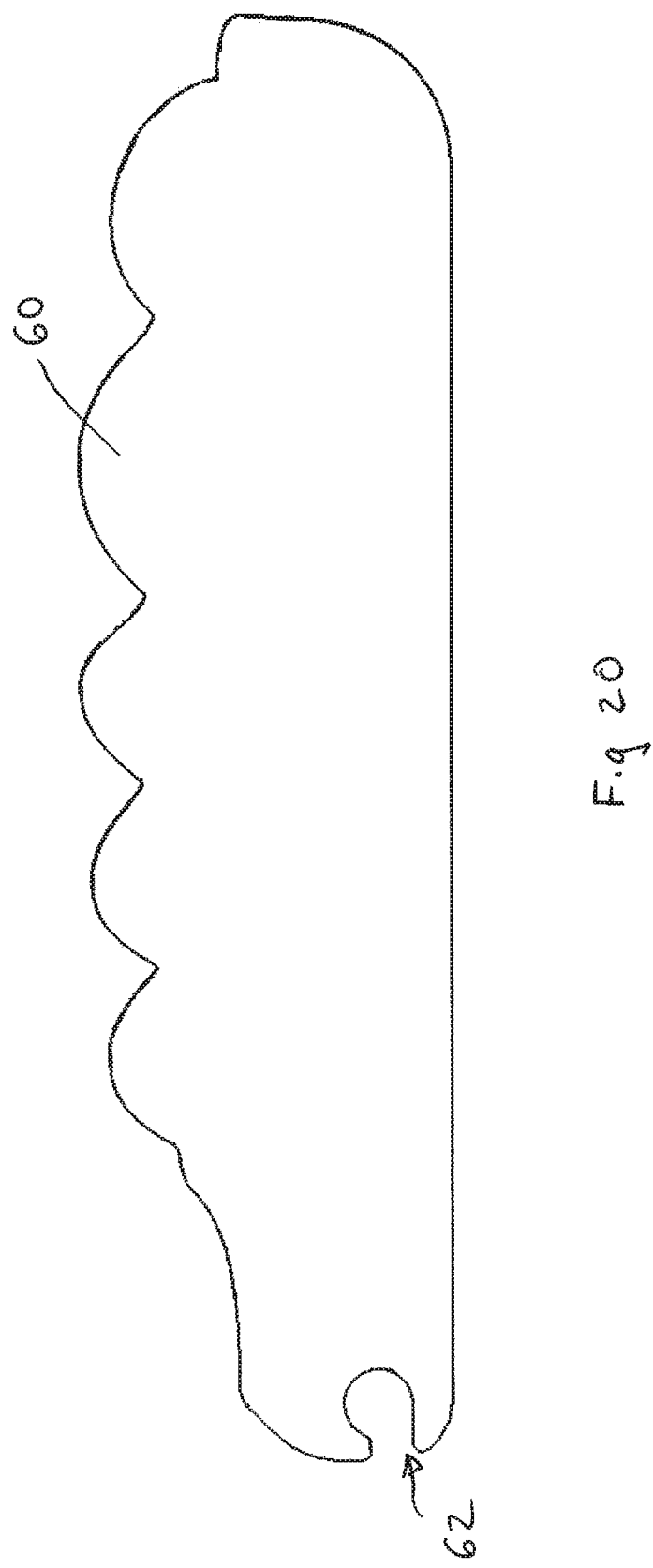
FIG. 20 shows a side view of the maxillary miniplast splint of the occlusal splint arrangement according to FIG. 19.

FIG. 20 shows a side view of the maxillary miniplast splint 59 of the occlusal splint arrangement 58 having the groove 62.

Figure 21:
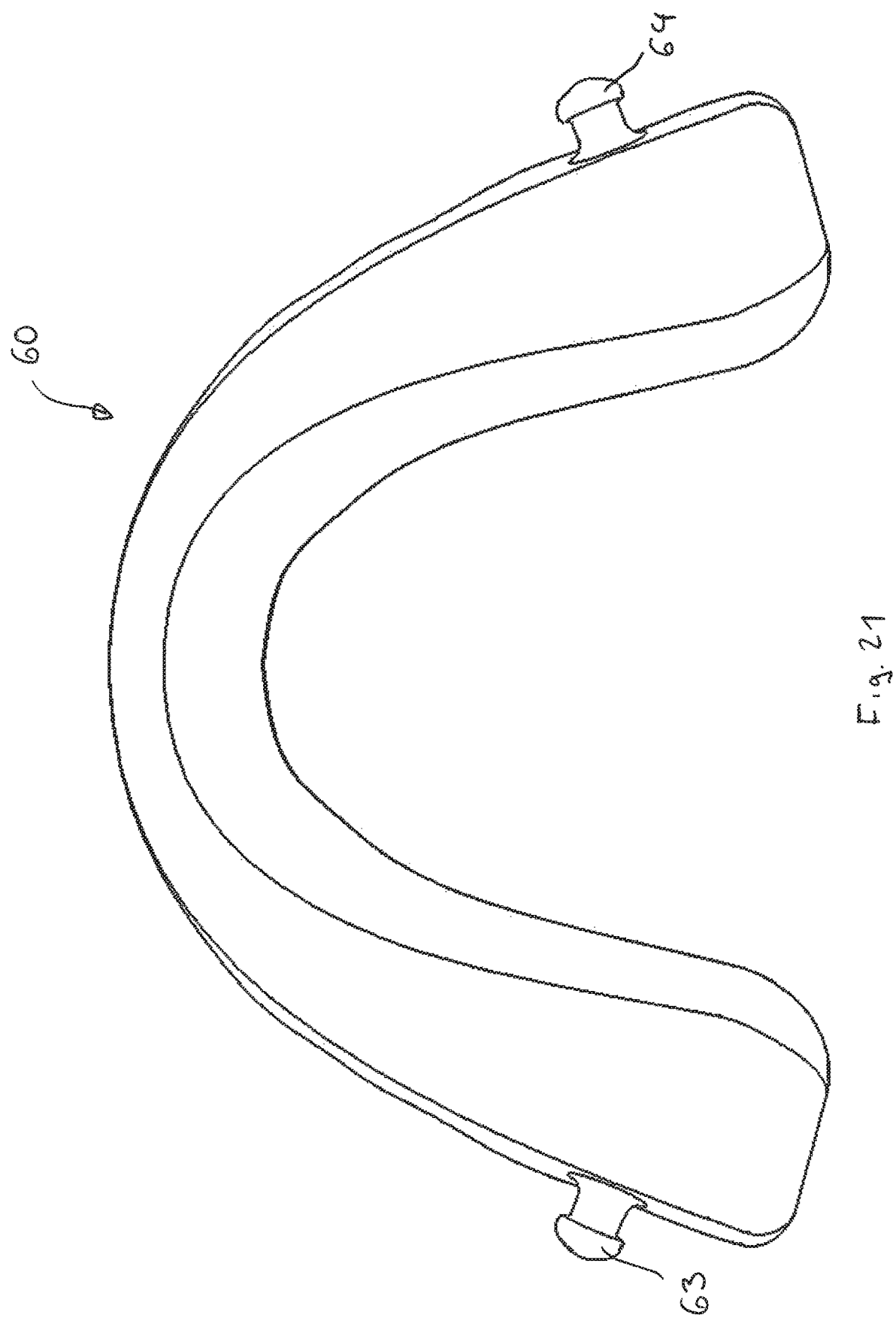
FIG. 21 shows a top view of the mandibular miniplast splint of the occlusal splint arrangement according to FIG. 19.

FIG. 21 shows a top view of the mandibular miniplast splint 60 having the fastening elements 63 and 64.

Figure 22:
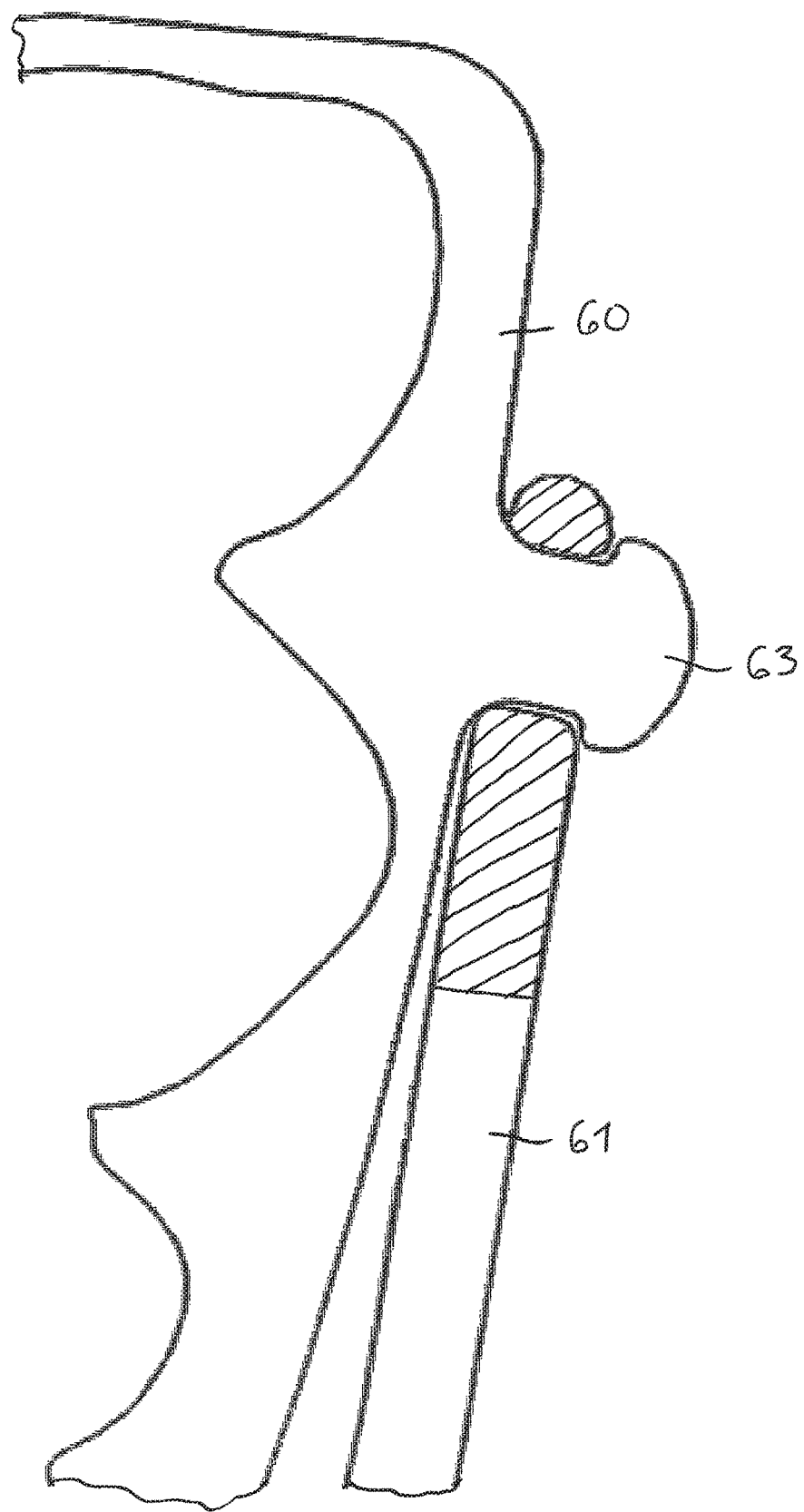
FIG. 22 shows a partial cross section of the fastening element of the mandibular miniplast splint according to FIG. 21 having the fixing band fixed thereon.

FIG. 22 shows a partial cross section of the fastening element 63 of the mandibular miniplast splint having a fixing band 61 fixed thereat.

Figure 23:
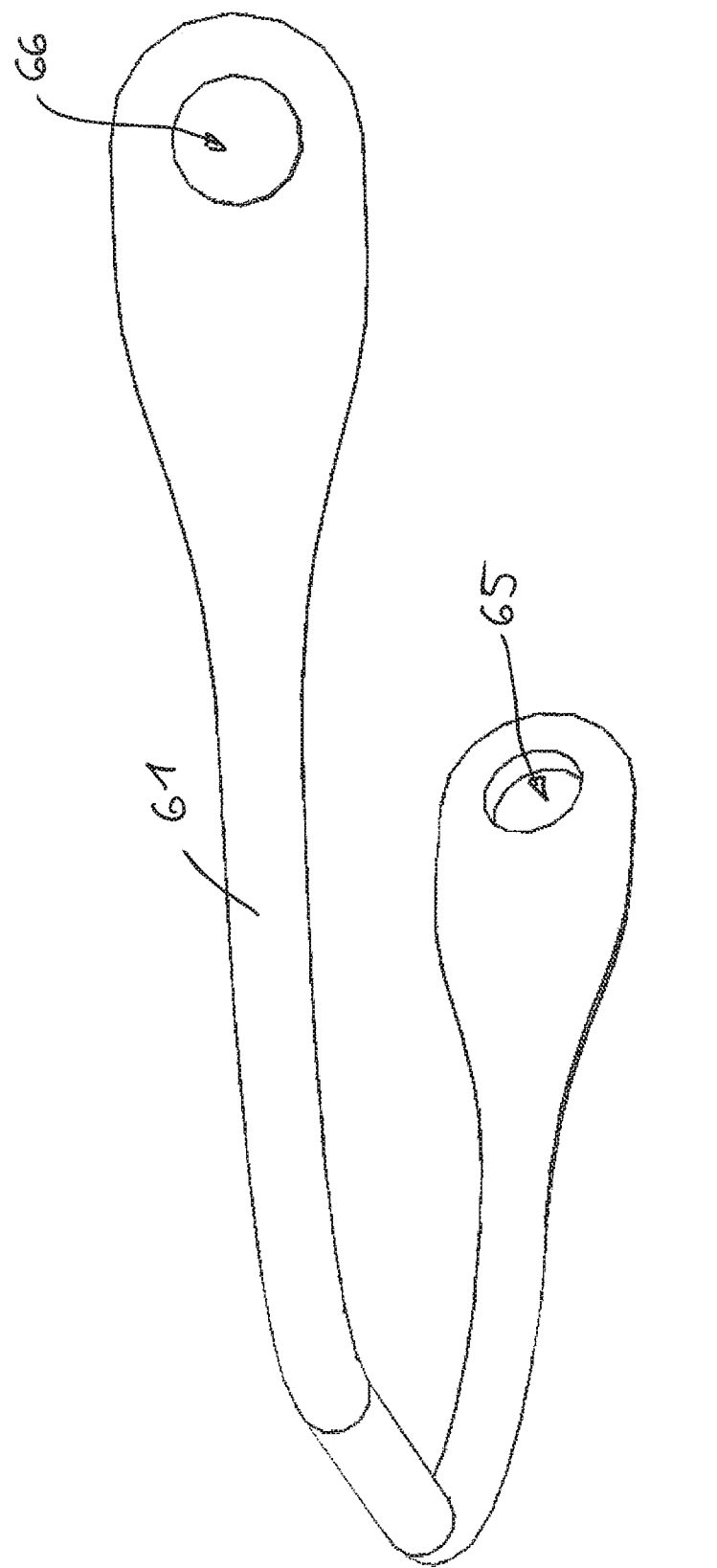
FIG. 23 shows a lateral perspective view of the preformed fixing band of the occlusal splint arrangement according to FIG. 19.

FIG. 23 shows a lateral perspective view of the preformed fixing band 61 of the occlusal splint arrangement 58 having the openings 65 and 66 for being hooked onto the fastening elements 63 and 64.

Figure 24:
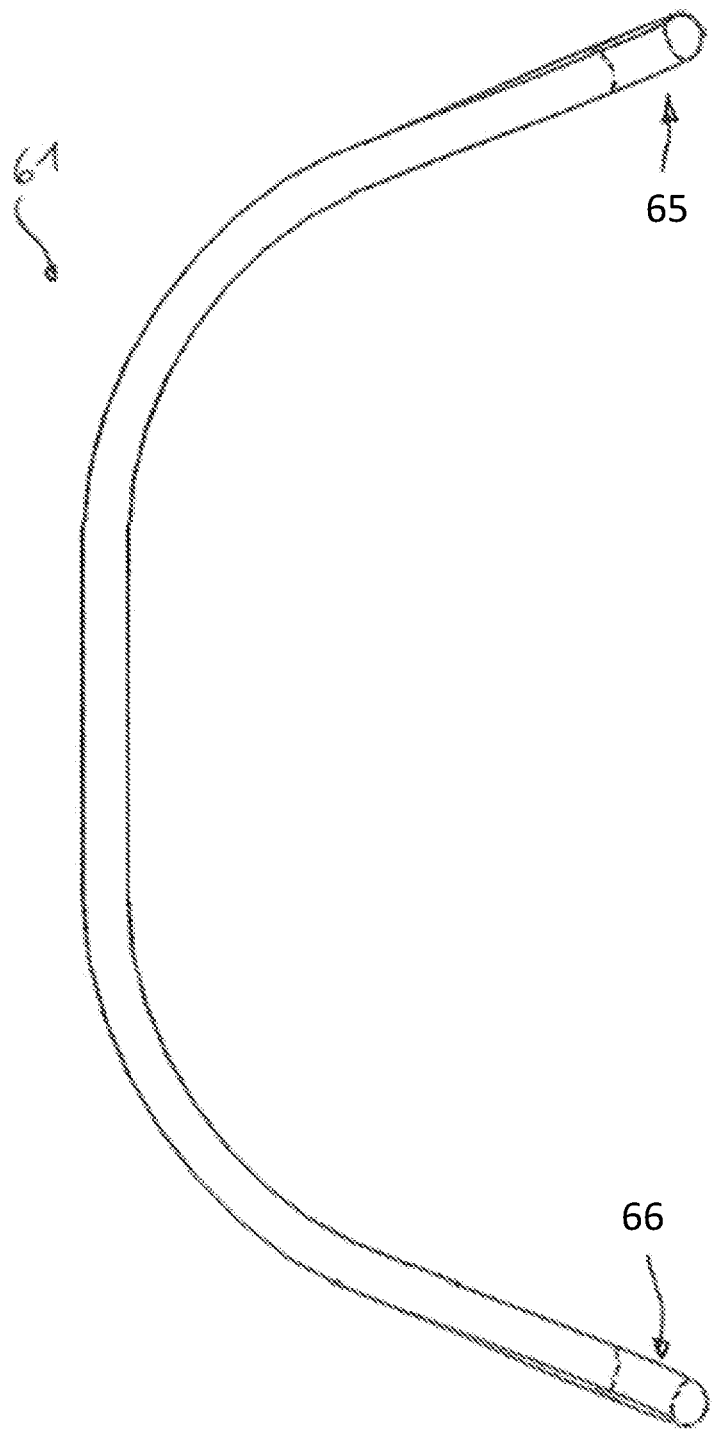
FIG. 24 shows a top view of the preformed fixing band according to FIG. 23.

FIG. 24 shows a top view of the preformed fixing band 58 having the openings 65 and 66 for being hooked onto the fastening elements 63 and 64.

LIST OF REFERENCE SIGNS 01 occlusal splint arrangement
02 maxillary miniplast splint
03 mandibular miniplast splint
04 transverse plane
05 fixing band
06 end (fixing band)
07 recess (fixing band)
08 fastening element
09 molar region
10 incisor region
11 guide means 12 middle section (fixing band)
13 groove
14 end (groove)
15 free length section (fixing band)
16 fixing pin
17 securing element
18 mandibular miniplast splint
19 cover element
20 smooth side surface (cover element)
21 opening (groove)
22 fixing web
23 fixing web
24 maxillary miniplast splint
25 groove
26 fixing band
27 maxillary miniplast splint
28 groove
29 guide means
30 fixing pin
31 upper side edge (groove)
32 lower side edge (groove)
33 occlusal splint arrangement
34 maxillary miniplast splint
35 mandibular miniplast splint
36 deflection element
37 fixing band
38 groove
39 fastening element
40 fixing band
41 projection
42 projection
43 end (fixing band)
44 opening (fixing band)
45 left fastening element
46 right fastening element
47 left end (fixing band)
48 fixing band
49 right end (fixing band)
50 opening (fixing band)
51 opening (fixing band)
52 preformed fixing band
53 maxillary miniplast splint
54 groove
55 fixing band
56 opening having the constriction
57 insertion chamfer
58 occlusal splint arrangement
59 maxillary miniplast splint
60 mandibular miniplast splint
61 fixing band
62 groove
63 fastening element
64 fastening element
65 opening
66 opening

The invention claimed is:

1. An occlusal splint arrangement having a maxillary splint to be disposed on the maxillary row of teeth and a mandibular splint to be disposed on the mandibular row of teeth, the mandibular splint being brought into contact with the maxillary splint in a transverse plane, and the mandibular splint being displaced labially in the x-direction and buccally in the y-direction in the transverse plane with respect to the maxillary splint, and the occlusal splint arrangement comprising a positioning means by means of which the position of the mandibular splint with respect to the maxillary splint is defined in the x-direction, wherein the positioning means is designed like a fixing band transmitting tensile forces, the two ends of the fixing band being fixed to two fastening elements, and the fastening elements being disposed in the left and the right molar region of the mandibular splint, and a middle section of the fixing band being guided at a guide means, in the form of a groove, and the groove being disposed in the incisor region of the maxillary splint, wherein the cross section of the groove is at least slightly smaller than the cross section of the fixing band, the fixing band being fixed in the groove by the press fit formed thereby and wherein the fixing band is made of an elastically deformable plastic material that is inherently stable along its length, the fixing band configured to be assembled to the splint and to accommodate the arcuate shape of the splint.

2. The occlusal splint arrangement according to claim 1, wherein the two fastening elements are integrally molded on or into the mandibular splint and/or in that the guide means is integrally molded on or into the maxillary splint.

3. The occlusal splint arrangement according to claim 2, wherein the two fastening elements are made of the same plastic material as the mandibular splint and/or in that the guide means is made of the same plastic material as the maxillary splint.

4. The occlusal splint arrangement according to claim 3, wherein the mandibular splint, together with the two fastening elements integrally molded thereon or thereinto, is produced in a 3D plastic printing process and/or in that the maxillary splint, together with the guide means integrally molded thereon or thereinto, is produced in a 3D plastic printing process.

5. The occlusal splint arrangement according to claim 3, wherein the mandibular splint, together with the two fastening elements integrally molded thereon or thereinto, is produced in a multi-axis milling process and/or in that the maxillary splint, together with the guide means integrally molded thereon or thereinto, is produced in a multi-axis milling process.

6. The occlusal splint arrangement according to claim 1, wherein the fixing band is adjustable in length.

7. The occlusal splint arrangement according to claim 1, wherein the fixing band is made of a plastic material.

8. The occlusal splint arrangement according to claim 1, wherein the fixing band is designed highly rigid in the direction of its longitudinal axis.

9. The occlusal splint arrangement according to claim 1, wherein the fixing band is designed elastically deformable transversely to its longitudinal axis.

10. The occlusal splint arrangement according to claim 1, wherein the groove is disposed labially in the incisor region of the maxillary splint and runs parallel to a dental arch, the groove at least partially accommodating the fixing band, and the fixing band transmitting compressive forces to the groove base.

11. The occlusal splint arrangement according to claim 10, wherein between each one of the two lateral ends of the groove in the maxillary splint and the respective one of the two fastening elements at the mandibular splint a distance is present, in which the fixing band runs unguided with a free length section, the two free length sections of the fixing band allowing a displacement of the mandibular splint with respect to the maxillary splint at least in the y-direction.

12. The occlusal splint arrangement according to claim 10, wherein between each one of the two lateral ends of the groove in the maxillary splint and the respective one of the two fastening elements at the mandibular splint a distance is present, a right and a left deflection element being provided at the mandibular splint, at which the fixing band is deflected and by which the vertical relative movement between the maxillary splint and the mandibular splint is limited.

13. The occlusal splint arrangement according to claim 10, wherein one or more constrictions are provided at an opening of the groove, by means of which the fixing band is fixed in a positive locking manner in the groove.

14. The occlusal splint arrangement according to claim 13, wherein at the outward facing side of the opening having the constriction an insertion chamfer is provided, by means of which the fixing band is guided into the groove.

15. The occlusal splint arrangement according to claim 10, wherein the width of the fixing band is larger than the opening cross section of the groove, the height of the fixing band being smaller than the opening cross section of the groove.

16. The occlusal splint arrangement according to clam 1, wherein the fixing band has a circular cross section.

17. The occlusal splint arrangement according to claim 1, wherein the fixing band has a rectangular cross section.

18. The occlusal splint arrangement according to claim 1, wherein the fixing band runs in the incisor region with the longitudinal side of the rectangular cross section parallel to the dental arch.

19. The occlusal splint arrangement according to claim 1, wherein the fastening elements at the mandibular splint are designed like fixing pins which project laterally in the right and the left molar region of the mandibular splint, the ends of the fixing band being hooked onto the fixing pins in a fixing manner.

20. The occlusal splint arrangement according to claim 19, wherein a securing element by means of which the fit of the fixing band at the fixing pin is secured, is provided at the free end of the fixing pins.

21. The occlusal splint arrangement according to claim 1, wherein smooth cover elements are provided adjacent to each fastening element at the mandibular splint, said cover elements projecting in the molar region of the mandibular splint and laterally covering the fastening elements at least partially.

22. The occlusal splint arrangement according to claim 1, wherein markings that indicate the position of the two splints with respect to each other are attached to the two splints.

* * * * *